US012778513B2

(12) United States Patent
Chang

(10) Patent No.: US 12,778,513 B2
(45) Date of Patent: Nov. 3, 2026

(54) PHYSIOLOGICAL SIGNAL FEATURE EXTRACTION METHOD AND PHYSIOLOGICAL SIGNAL FEATURE EXTRACTION DEVICE THEREOF

(71) Applicant: Wistron Corporation, New Taipei City (TW)

(72) Inventor: Hsuan-Tsung Chang, New Taipei City (TW)

(73) Assignee: Wistron Corporation, New Taipei City (TW)

( * ) Notice: Subject to any disclaimer, the term of this patent is extended or adjusted under 35 U.S.C. 154(b) by 1107 days.

(21) Appl. No.: 17/895,052

(22) Filed: Aug. 24, 2022

(65) Prior Publication Data

US 2023/0293112 A1 Sep. 21, 2023

(30) Foreign Application Priority Data

Mar. 15, 2022 (TW) .................................. 111109337

(51) Int. Cl.
*A61B 5/00* (2006.01)
*A61B 5/024* (2006.01)

(52) U.S. Cl.
CPC ........ *A61B 5/7246* (2013.01); *A61B 5/02416* (2013.01); *A61B 5/7214* (2013.01); *A61B 5/7278* (2013.01); *A61B 5/6816* (2013.01)

(58) Field of Classification Search
CPC .............. A61B 5/7246; A61B 5/02416; A61B 5/7214; A61B 5/6816; A61B 5/02125;
(Continued)

(56) References Cited

U.S. PATENT DOCUMENTS

2006/0224074 A1* 10/2006 Ouchi .................. A61B 5/4812 600/513
2013/0332773 A1* 12/2013 Yuan .................. G05B 23/0205 714/E11.178

(Continued)

FOREIGN PATENT DOCUMENTS

CN 203970364 U * 12/2014
CN 108306736 A 7/2018

(Continued)

OTHER PUBLICATIONS

Tur ,Basal Perfusion of the Cutaneous Microcirculation: Measurements as a Function of Anatomic Position ,1983.

(Continued)

*Primary Examiner* — Yossef Korang-Beheshti
(74) *Attorney, Agent, or Firm* — Winston Hsu

(57) ABSTRACT

A physiological signal feature extraction method includes receiving a physiological signal, determining in a situation that a second pulse in a plurality of pulses of the physiological signal being correlated to a first pulse in the plurality of pulses, selecting the second pulse as one of a plurality of reference pulses in a reference waveform sequence after the second pulse is determined as correlated to the first pulse, averaging the plurality of reference pulses into a template pulse, performing match comparison on the plurality of pulses by the template pulse one by one, and extracting a plurality of features from each of the plurality of pulses that matches the template pulse.

18 Claims, 8 Drawing Sheets

(58) Field of Classification Search
CPC ................ A61B 5/7221; A61B 5/7267; A61B 5/0059; A61B 5/02; A61B 5/6803; A61B 5/72
See application file for complete search history.

(56) References Cited

U.S. PATENT DOCUMENTS

| | | | | |
|---|---|---|---|---|
| 2014/0135636 | A1 | 5/2014 | Kang | |
| 2019/0057166 | A1 * | 2/2019 | Liongosari ........... | B60N 2/0278 |
| 2020/0138305 | A1 | 5/2020 | Mukkamala | |
| 2023/0000444 | A1 * | 1/2023 | Jang ..................... | A61B 5/0205 |

FOREIGN PATENT DOCUMENTS

| | | | | |
|---|---|---|---|---|
| CN | 110731762 | A | 1/2020 | |
| CN | 111870237 | A | 11/2020 | |
| CN | 113365553 | A | 9/2021 | |
| CN | 113539522 | A | 10/2021 | |
| WO | WO-2021051873 | A1 * | 3/2021 | ............... A61B 5/72 |

OTHER PUBLICATIONS

Karlen ,Photoplethysmogram signal quality estimation using repeated Gaussian filters and cross-correlation ,2012.
Wong ,An evaluation of the cuffless blood pressure estimation based on pulse transit time technique: a half year study on normotensive subjects ,2009.

* cited by examiner

PHYSIOLOGICAL SIGNAL FEATURE EXTRACTION METHOD AND PHYSIOLOGICAL SIGNAL FEATURE EXTRACTION DEVICE THEREOF

BACKGROUND OF THE INVENTION

1. Field of the Invention

The present invention relates to a physiological signal feature extraction method and a physiological signal feature extraction device thereof, and more particularly, to a physiological signal feature extraction method and a physiological signal feature extraction device thereof for screening/sorting signal waveforms to improve signal analysis accuracy.

2. Description of the Prior Art

Photoplethysmography (PPG) may non-invasively detect the volume change of blood, and thus measure physiological indexes such as heart rates or blood oxygen concentration. Sensing elements of Photoplethysmography mainly include light-emitting diodes and photodiodes. The light-emitting diodes emit light, and the photodiodes receive light signals passing through vessels. The alternating current (AC) component of the light signal is associated with blood changes caused by heart beats, and the direct-current (DC) component of the light signal is associated with unchanged light absorption of subcutaneous tissues, venous blood, etc.

The light signals measured by Photoplethysmography are extremely susceptible to the interference of external noise. Low-frequency noise mostly comes from motion and breathing, which causes amplitude drift in the DC component. High-frequency noise is mostly due to ambient light, which causes disturbances in the AC component.

The blood vessel perfusion value of ear with dense micro-vessels is higher than that of hand, meaning that blood pressure measurement near earlobe has a higher accuracy. However, it is difficult to visually see whether a measurement device is properly worn or whether the wearing position is bad. It is easy to cause light to scatter or the photodiode(s) to receive noise including external light because sensor(s) of the measurement device may not be closely attached to the ear of a user.

There is still room for improvement in terms of the prior art.

SUMMARY OF THE INVENTION

It is therefore an objective of the present invention to provide a physiological signal feature extraction method and a physiological signal feature extraction device thereof which is able to screen/filter signal waveforms to improve signal analysis accuracy.

An embodiment of the present invention discloses a physiological signal feature extraction method comprising receiving a physiological signal, wherein the physiological signal comprises a plurality of pulses; determining in a situation that a second pulse in the plurality of pulses being correlated to a first pulse in the plurality of pulses; selecting the second pulse as one of a plurality of reference pulses in a reference waveform sequence after the second pulse is determined as correlated to the first pulse; averaging the plurality of reference pulses out to a template pulse; performing match comparison on the plurality of pulses by the template pulse respectively; and extracting a plurality of features from each of the plurality of pulses matching the template pulse.

An embodiment of the present invention discloses a physiological signal feature extraction device comprising a processing circuit, configured to execute a program code; and a storage circuit, coupled to the processing circuit and configured to store the program code, wherein the program code comprises receiving a physiological signal, wherein the physiological signal comprises a plurality of pulses; determining in a situation that a second pulse in the plurality of pulses being correlated to a first pulse in the plurality of pulses; selecting the second pulse as one of a plurality of reference pulses in a reference waveform sequence after the second pulse is determined as correlated to the first pulse; averaging the plurality of reference pulses out to a template pulse; performing match comparison on the plurality of pulses by the template pulse respectively; and extracting a plurality of features from each of the plurality of pulses matching the template pulse.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
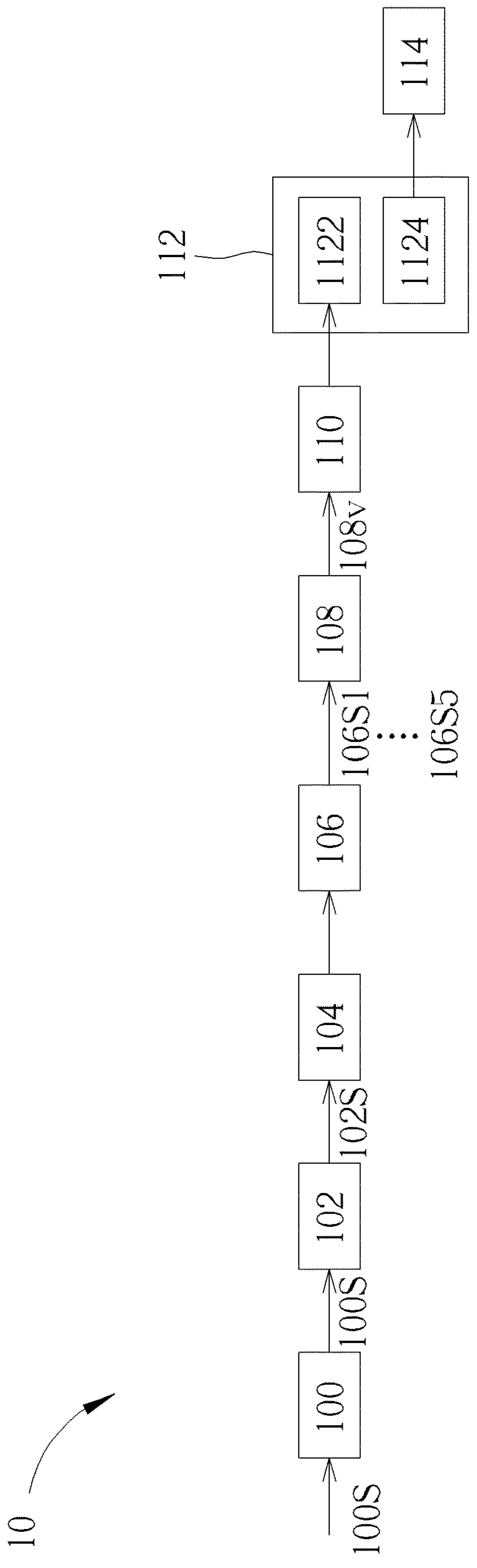
FIG. 1 is a schematic diagram of a signal feature extraction device according to an embodiment of the present invention.

FIG. 1 is a schematic diagram of a signal feature extraction device 10 according to an embodiment of the present invention. The signal feature extraction device 10 is able to screen/filter/sort the waveform(s) of (physiological) signal(s) received by the signal feature extraction device 10 to ensure that the waveform(s) of the signal(s) for (subsequent) interpretation are well-shaped/good/correct and to avoid using abnormal waveforms for signal analysis, thereby improving the accuracy of signal analysis.

For example, the signal feature extraction device 10 may be utilized for an ear-clip physiological measurement device (such as a Thor ear-clip device). The ear-clip physiological measurement device may be in contact with the wall of an ear. The ear-clip physiological measurement device may include a Photoplethysmography module for transmitting and receiving optical signals to generate a (physiological) signal 100S. Since the systole and diastole of a heart may lead to pulsations and cause changes in vascular volume, heme with oxygen and heme without oxygen in the blood may change accordingly, which may affect the degree of light absorption. Therefore, intensities of lights received by the Photoplethysmography module are different, and the signal 100S output by the Photoplethysmography module may include an AC component. The signal feature extraction device 10 may screen the waveform of the signal 100S to ensure that the waveform(s) of signal(s) for subsequent analysis is well-shaped rather than abnormally-shaped, such that the signal 100S may be used to estimate blood pressure accurately.

As shown in FIG. 1, the signal feature extraction device 10 may include an input module 100, a preprocessing module 102, a local extreme value detection module 104, a waveform segmentation module 106, a template initialization module 108, a template matching module 110, a calculation module 112, and an output module 114.

The input module 100 may receive the signal 100S from the ear-clip physiological measurement device. For example, the input module 100 may include a transmission module to transmit the signal 100S through wireless communication such as Bluetooth or WiFi or through a transmission line.

The preprocessing module 102 may process the signal 100S to generate a preprocessed signal 102S. In one embodiment, the preprocessing module 102 may normalize the signal 100S according to the mean value or the standard deviation of the signal 100S, such that the displacement/magnitude of the signal 100S may fall between −1 and 1 (and the amplitude of the signal 100S may be 1).

In one embodiment, an accelerometer of the ear-clip physiological measurement device may determine whether a subject/testee is in a static state, and the preprocessing module 102 may perform corresponding signal processing accordingly. For example, the preprocessing module 102 may filter/sort out the waveform(s) of certain pulse(s) when the subject is not in a static state, and thus pulse wave feature(s) is/are not extracted from the pulse(s). Alternatively, the preprocessing module 102 may not process the signal 100S, and the output module 114 requests the subject to perform the measurement again.

In one embodiment, the preprocessing module 102 may include a band-pass filter to perform band-pass filtering on the signal 100S. The preprocessing module 102 may filter out high-frequency noise or ambient light noise to make waveform(s) smoother and improve the signal-to-noise ratio (SNR), thereby enabling the signal feature extraction device 10 to calculate/analyze more accurately. In one embodiment, the band-pass filter may be a Butterworth filter, and its cut-off frequency band may be 0.5 hertz (Hz) to 5 Hz.

Figure 2:
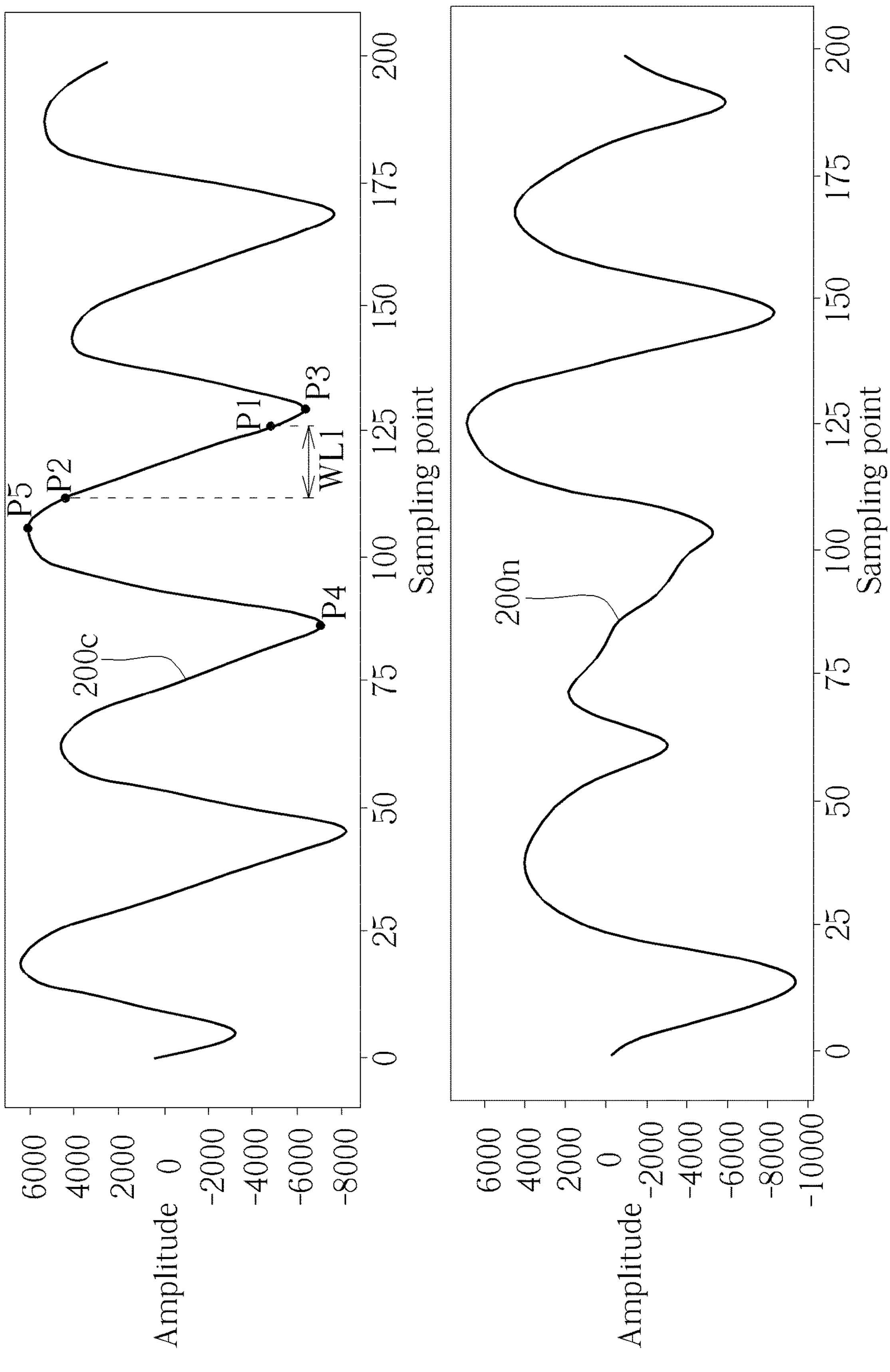
FIG. 2 is a schematic diagram of preprocessed signals according to an embodiment of the present invention.

In one embodiment, the preprocessing module 102 may process the signal 100S to output the preprocessed signal 102S including only the AC component. FIG. 2 is a schematic diagram of preprocessed signals 200*c* and 200*n* according to an embodiment of the present invention. In FIG. 2, the sampling rate may be 50 points per second so that the interval between two adjacent sampling points may be 20 milliseconds (ms). The preprocessed signal 102S may be implemented by the preprocessed signal 200*c* or 200*n*. The preprocessed (physiological) signals 200*c*, 200*n*, 102S (or the (physiological) signal 100S) may be a periodic pulse wave and may include multiple pulses. The preprocessed signals 200*c* or 200*n* may present a continuous waveform measured from one subject at different times. As shown in FIG. 2, the waveform of the preprocessed signal 200*c* is better than that of the preprocessed signal 200*n*. The waveform of the preprocessed signal 200*n* may be disturbed and thus shaped abnormally. Consequently, the waveform of the preprocessed signal 200*c* is more suitable for pulse wave feature extraction to capture pulse wave feature(s) of the pulse wave, and only part of the waveform of the preprocessed signal 200*n* is suitable for pulse wave feature extraction. The signal feature extraction device 10 of the present invention may remove/ignore abnormal pulse waveform(s) in the preprocessed signal 200*n*, and extract pulse wave feature(s) from well-shaped pulse waveform(s) in the preprocessed signal 200*n*.

The local extreme value detection module 104 may search for local extrema/extremum (such as a maximum or minimum) using a window of a variable length. The local extreme value detection module 104 may firstly adopt one certain window length (e.g., a window length WL1), and then dynamically adjust/extend/shorten the window length according to a sampling point of a relatively low value (e.g., a sampling point P1) and a sampling point of a relatively high value (e.g., a sampling point P2), which are found by the local extreme value detection module 104, so as to determine/find sampling point(s) of local/relative minimum value(s) of the waveform (such as troughs P3 and P4 of the waveform) and sampling point(s) of local/relative maximum value(s) (such as a peak P5 of the waveform). In one embodiment, the window length WL1 may correspond to a (general) heart rate. The window length WL1 may be, for example, 1 second, but is not limited thereto.

Figure 3:
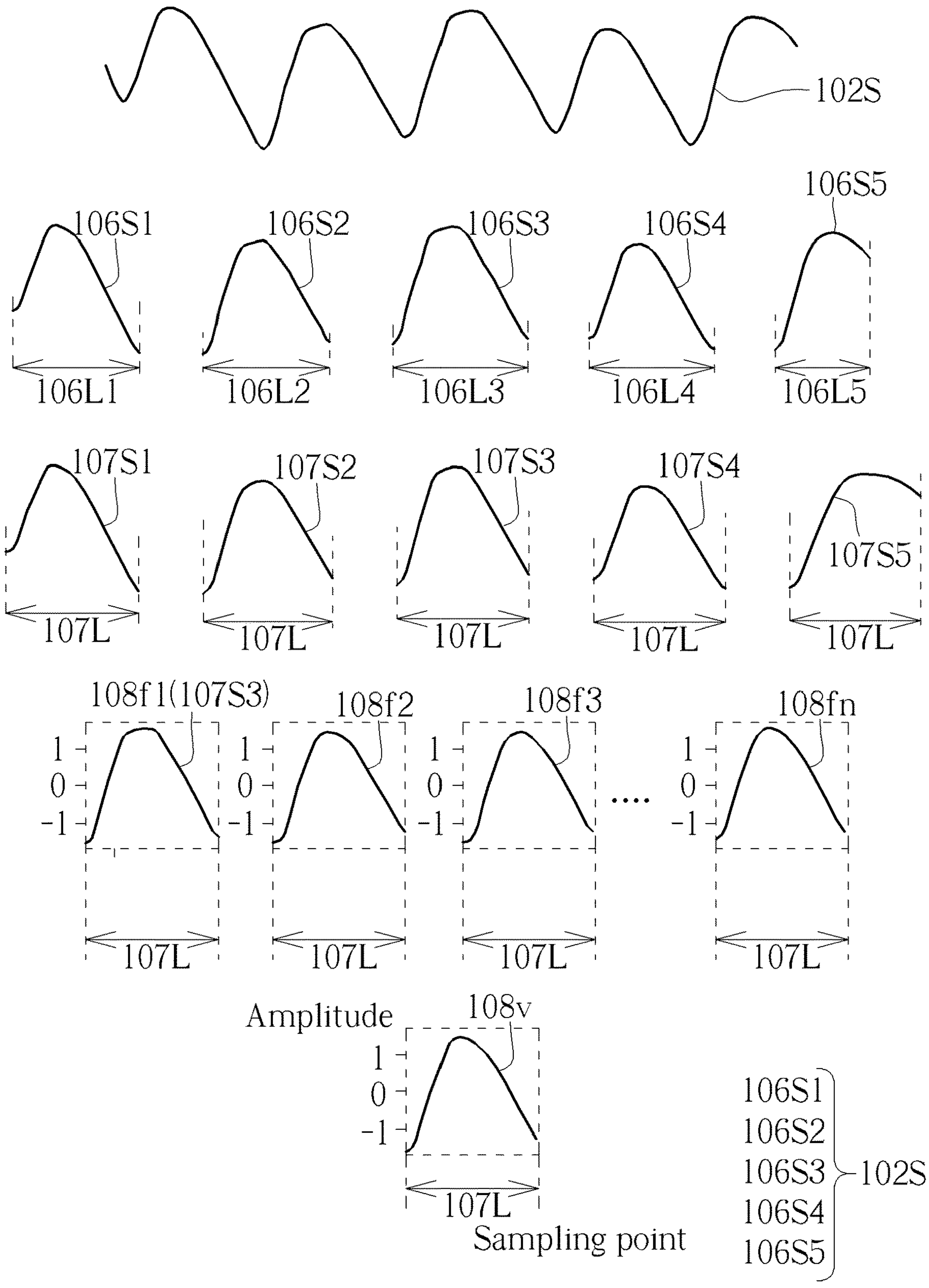
FIG. 3 is a schematic diagram of a signal processing procedure according to an embodiment of the present invention.

The waveform segmentation module 106 may divide the waveform based on the position of the trough(s) (or the peak(s)) and extract pulse(s) from the periodic pulse wave. For example, FIG. 3 is a schematic diagram of a signal processing procedure according to an embodiment of the present invention. As shown in FIG. 3, the waveform segmentation module 106 may segment the preprocessed signal 102S into pulses 106S1-106S5. The sampling rate may be 50 points per second, such that the interval between two adjacent sampling points may be 20 milliseconds.

In one embodiment, since pulse time lengths 106L1-106L5 of the pulses 106S1-106S5 of the preprocessed signal 102S may not be equal in length (for example, the pulse time length 106L3 of the pulse 106S3 may be longer than the pulse time length 106L4 of the pulse 106S4), the waveform segmentation module 106 may convert/change from the pulses 106S1-106S5 into pulses 107S1-107S5 respectively to facilitate (subsequent) processing. As a result, the pulses 107S1-107S5 may have the same pulse duration 107L, meaning that lengths of time of pulses are normalized. In one embodiment, the waveform segmentation module 106 may make the pulse duration 107L of the pulses 107S1-107S5 equal to the median of the pulse time lengths 106L1-106L5 or another length of time which is not extremely long or short (e.g., the arithmetic mean of the pulse time lengths 106L1-106L5, the geometric mean of the pulse time lengths 106L1-106L5, the harmonic mean of the pulse time lengths 106L1-106L5, or the root mean square of the pulse time lengths 106L1-106L5). In one embodiment, the pulse duration 107L of the pulses 107S1-107S5 may be equal to the mode of the pulse time lengths 106L1-106L5.

In one embodiment, the waveform segmentation module 106 may normalize the pulses 106S1-106S5 to adjust the pulse time lengths 106L1-106L5 of the pulses 106S1-106S5. The waveform segmentation module 106 may perform down-sampling (to reduce the number of sampling points) for longer pulse(s) (e.g., the pulse 106S3), and may perform up-sampling (e.g., using interpolation or linear interpolation to increase the number of sampling points) for shorter pulse(s) (e.g., the pulse 106S1), such that the pulses 107S1-107S5 have the same pulse duration 107L (alternatively, the pulses 107S1 to 107S5 have the same number of sampling points). In one embodiment, the waveform segmentation module 106 may leverage linear interpolation: The waveform segmentation module 106 may take two adjacent sampling points in a pulse (e.g., the pulse 106S1) to calculate/yield a linear equation and insert desired number of sampling points satisfying the linear equation, such that the pulse time lengths of the pulses 107S1 to 107S5 is equal to the desired normalized pulse duration 107L. In one embodiment, the waveform segmentation module 106 may avoid removing certain critical sample point(s) (e.g., peak(s), trough(s), or inflection point(s)) during down-sampling: The waveform segmentation module 106 may eliminate/delete less critical sample point(s).

Although the preprocessing module 102 may filter out high-frequency noise, there may still be noise with a frequency band similar to a heart rate (such as noise generated by motion). Accordingly, the present invention utilizes the template initialization module 108 or the template matching module 110 to screen/assess each pulse of a periodic pulse wave one by one to select well-shaped pulse(s).

The template initialization module 108 may choose some of the pulses to form a reference waveform sequence, and average out all the pulses of the reference waveform sequence to output a template pulse. The template pulse after average may improve the stability and error tolerance of algorithm. When a waveform in poor shape is mistakenly selected by the template initialization module 108 to constitute a reference waveform sequence, averaging out all the pulses in the reference waveform sequence may reduce error and achieve risk distribution. For example, the template initialization module 108 may select the pulse 107S3 (serving as a pulse **108*f*1) to form a reference waveform sequence including other pulses 108*f*2-108*fn* having been selected, and average the pulses 108*f*1-108*fn* out at the template pulse 108*v*. As a result, the waveform of the template pulse 108*v* output from the template initialization module 108 is more ideal. Even though the waveform of the pulse 108*f*1 is gentler in the vicinity of its peak than that of any the pulses 108*f*2 to 108*fn*, averaging out the waveforms of the pulses 108*f*1-108*fn* may make the template pulse 108*v* representative of the pulses 108*f*1-108*fn*. The waveform of the template pulse 108*v* may thus be treated or regarded as the standard pulse waveform of the subject. Averaging out the waveforms of the pulses 108*f*1-108*fn* refers to calculating the average of the amplitudes of the pulses 108*f*1-108*fn* at each sampling point one by one to obtain the corresponding amplitudes of the template pulse 108*v*** at all sampling points.

In one embodiment, the template initialization module 108 may select pulse(s) according to similarity/correlation. Based on the periodicity of the pulse wave, the template initialization module 108 may compare a previous pulse (e.g., the pulse 107S2 captured in the previous sampling interval) with a pulse under analysis (e.g., the pulse 107S3 captured in the current sampling interval) one by one. If the previous pulse (e.g., the pulse 107S2) bears high similarity/correlation to the pulse under analysis (e.g., the pulse 107S3), the waveform of the pulse under analysis may be stable and representative, and thus the pulse under analysis may be selected as a reference pulse in the reference waveform sequence. In one embodiment, if the cross-correlation coefficient between the previous pulse (referred to as a first pulse) and the pulse under analysis (referred to as a second pulse) is greater than or equal to a similarity threshold (for example, 0.9, but not limited to), it is determined that the previous pulse (e.g., the pulse 107S2) is similar/correlated to the pulse under analysis (e.g., the pulse 107S3), and the pulse under analysis (e.g., the pulse 107S3) may be added to the reference waveform sequence. The higher the similarity threshold is set, the more accurate the calculation would be. However, as the similarity threshold grows, the subject is required to wear the signal feature extraction device 10 more correctly/properly, and the (measurement) waiting time of measurement would be longer. In one embodiment, the similarity threshold may be in a range of 0.8 to 0.9 to ensure a sufficient degree of screening.

In one embodiment, as shown in FIG. 3, the reference waveform sequence may include pulses **108*f*1-108*fn* (referred to as reference pulses). In one embodiment, the upper limit of the number of pulses in the reference waveform sequence may be set to a preset pulse number. The preset pulse number may be, for example, equal to 5 (namely, n=5). However, the present invention is not limited thereto, and the preset pulse number may be in a range of 3 to 20. When the number of the pulses selected by the template initialization module 108 reaches the preset pulse number (e.g., 5), the template initialization module 108 may suspend the comparison between the previous pulse and the pulse under analysis and average out the five reference pulses, which have been saved in and constitute the reference waveform sequence, to output template pulse 108*v***. The larger the number of pulses of the reference waveform sequence, the longer the measurement waiting time of the subject. Accordingly, the number of pulses of the reference waveform sequence may not be too large.

In one embodiment, the pulses **108*f*1-108*fn* may not necessarily be consecutive pulses in the preprocessed signal 102S. Each of the pulses 108*f*1-108*fn* respectively is highly similar/correlated to the corresponding one or more previous pulse in the preprocessed signal 102S; however, the pulses 108*f*1-108*fn* may not be continuous pulses. In other words, the pulse 108*f*1 may be the pulse 107S3 (when the pulse 107S3 is highly similar/correlated to the pulse 107S1 or 107S2), but the pulse 108*f*2 may not be the pulse 107S4, which is the previous pulse of the pulse 107S3 according to the preprocessed signal 102**S.

In one embodiment, the template initialization module 108 may compare a previous pulse (e.g., the pulse 107S2 captured in the previous sampling interval) with a pulse under analysis (e.g., the pulse 107S3 captured in the current sampling interval). Alternatively, the template initialization module 108 may compare a more previous pulse (e.g., the pulse 107S1 captured in a more previous sampling interval) with a pulse under analysis (e.g., the pulse 107S3 captured in the current sampling interval).

In one embodiment, the pulse time lengths of the pulses **108*f*1-108*fn* and the pulse time length of the template pulse 108*v* may be equal to the normalized pulse duration 107L. That is to say, the signal feature extraction device 10 may make the pulse time length of the previous pulse (e.g., the pulse 107S2) equal to the pulse time length of the pulse under analysis (e.g., the pulse 107S3**) before the cross-correlation coefficient between the previous pulse and the pulse under analysis is calculated or subsequent processing (such as average) is performed.

Figure 4:
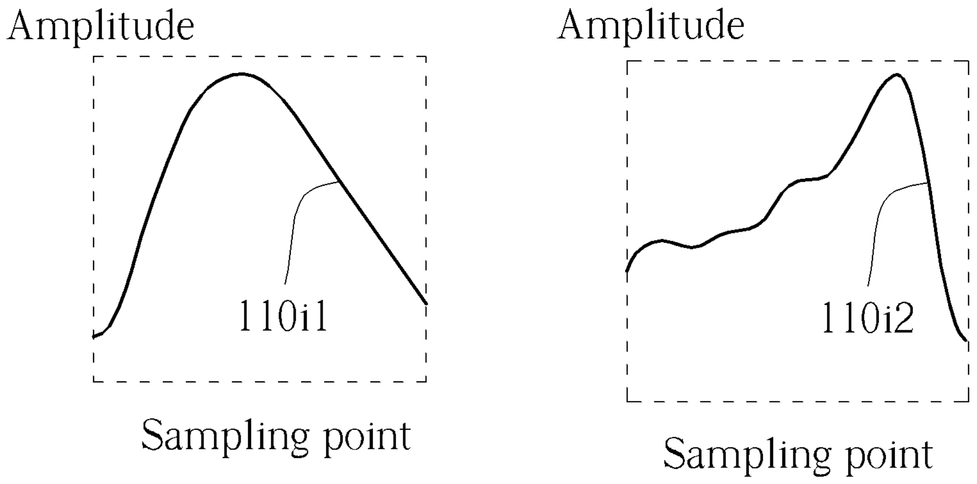
FIG. 4 to FIG. 6 are schematic diagrams of pulses according to embodiments of the present invention.

The template matching module 110 may compare each pulse (e.g., the pulses 107S1-107S5) in the measurement time for the subject to be measured with the template pulse **108*v*. If the pulse being compared has a high similarity/correlation to the template pulse 108*v*, the template matching module 110 may perform feature extraction on the pulse being compared. In one embodiment, the template matching module 110 may measure the cross-correlation coefficient between the pulse being compared (e.g., the pulse 107S1) and the template pulse 108*v*. If the cross-correlation coefficient is greater than or equal to a match threshold (for example, 0.9, but not limited thereto), the template matching module 110 may determine that the pulse being compared matches the template pulse 108*v* and extract feature(s) from the pulse being compared. In one embodiment, the match threshold may be in a range of 0.8 to 0.9 to ensure a sufficient degree of screening. For example, FIG. 4 is a schematic diagram of pulses 110*i*1 and 110*i*2 according to an embodiment of the present invention. The template matching module 110 may compare the pulse 110*i*1 or 110*i*2 with the template pulse 108*v*. Since the pulse 110*i*1 is more similar/correlated to the template pulse 108*v* (e.g., the peaks of the pulse 110*i*1 and the template pulse 108*v* may be approximately aligned/coincided and the slopes of the pulse 110*i*1 and the template pulse 108*v* may be approximately similar/correlated with respect to all the sampling points) than the pulse 110*i*2, feature(s) of the pulse 110*i*1 may be extracted/elicited by the template matching module 110**.

Figure 5:
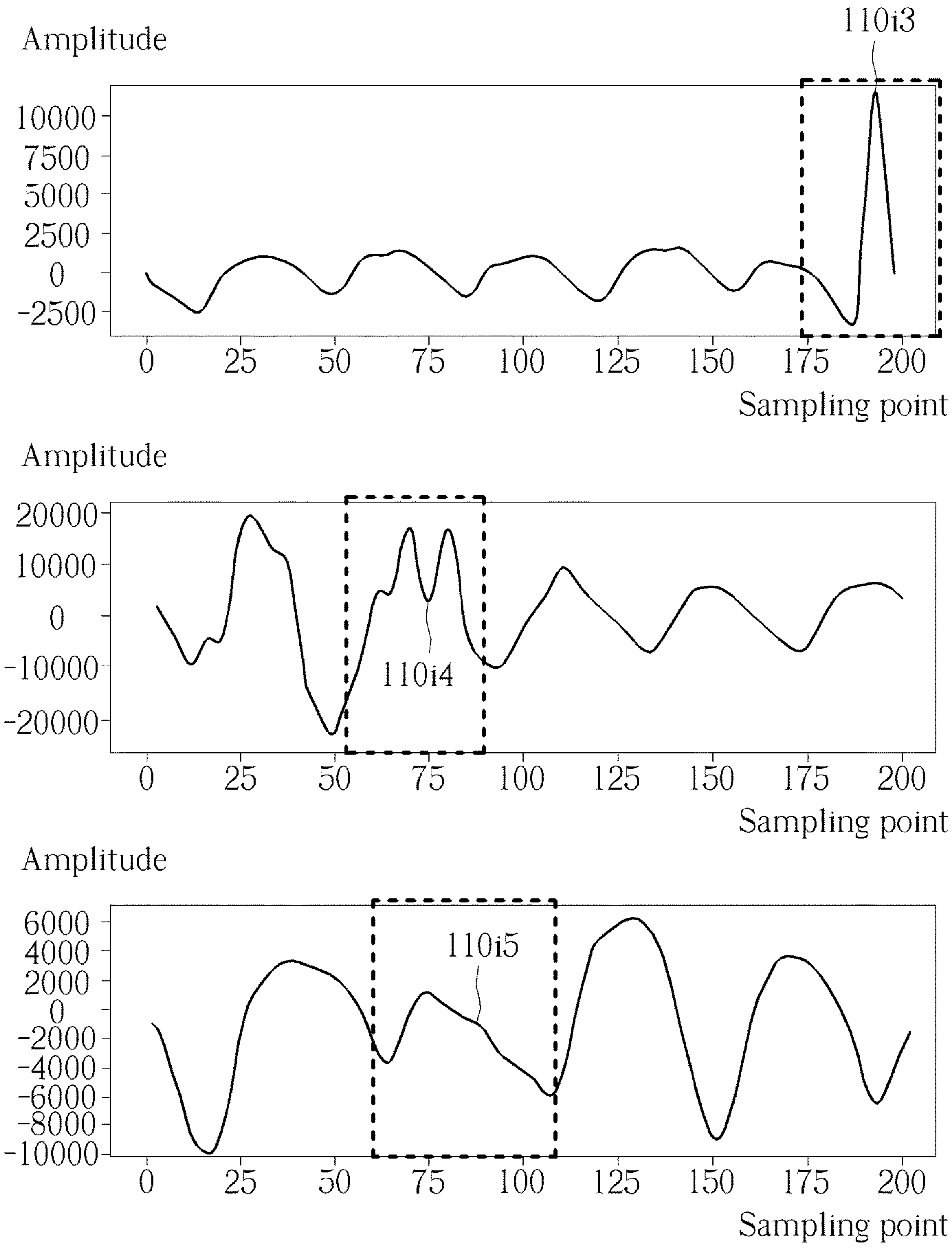

If the template matching module 110 determines that the similarity/correlation between the pulse being compared and the template pulse **108*v* is low, the template matching module 110 may not perform feature extraction on the pulse being compared or filter out the pulse being compared. For example, in FIG. 4, if the template matching module 110 determines that the similarity/correlation between the pulse 110*i*2 and the template pulse 108*v* is relatively low, the template matching module 110 may not extract feature(s) from the pulse 110*i*2. For example, FIG. 5 is a schematic diagram of pulses 110*i*3-110*i*5 according to an embodiment of the present invention. In FIG. 5, the sampling rate may be 50 points per second, such that the interval between two adjacent sampling points may be 20 milliseconds. The pulse 110*i*3 may be a surge with abnormally high amplitude. The pulse 110*i*4 may have double peaks because of arrhythmia. The waveform of the pulse 110*i*5 may have an abnormally short systole. In one embodiment, since each of the pulses 110*i*3-110*i*5 (with respect to another pulse preceding or following the one of the pulses 110*i*3-110*i*5) has an abnormal waveform in its corresponding continuous waveform, the cross-correlation coefficient between the one of the pulses 110*i*3-110*i*5 and the template pulse 108*v* (or the waveform of another pulse preceding or following the one of the pulses 110*i*3-110*i*5) is lower than the match threshold. As a result, the pulses 110*i*3-110*i*5 may be filtered out and may not be used for feature extraction, while the waveforms of other pulses may be extracted to obtain pulse wave features. In other words, the signal feature extraction device 10** of the present invention may ignore/abandon abnormal pulse waveform(s) and extract pulse wave feature(s) from other well-shaped pulses in a signal.

The calculation module 112 may leverage statistics or machine learning (e.g., linear regression or neural network model) methods to choose parameters for building, for instance, a model of blood pressure estimation. The calculation module 112 may include a feature extraction unit 1122 and a calculation unit 1124.

Figure 6:
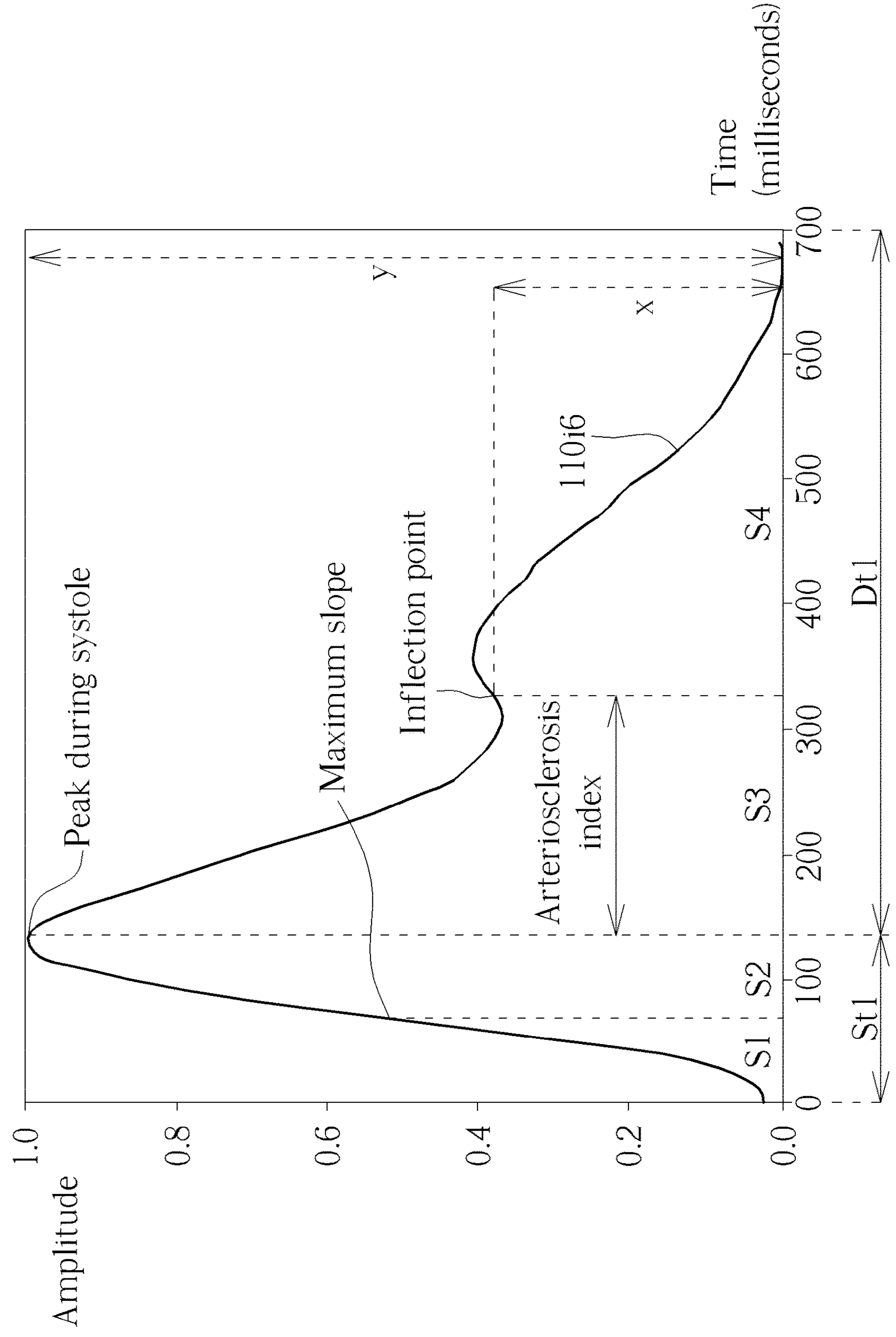

The feature extraction unit 1122 may perform feature extraction on certain pulses according to instruction of the template matching module 110. For example, FIG. 6 is a schematic diagram of a pulse **110*i*6 according to an embodiment of the present invention. The feature extraction unit 1122 may extract feature(s) such as a systolic pulse wave area (i.e., the sum of areas S1 and S2), a diastolic pulse wave area (i.e., the sum of areas S3 and S4), a pulse wave area (i.e., the sum of the areas S1-S4), a heart rate, a systolic time St1, a diastolic time Dt1, a maximum pulse wave amplitude, a minimum pulse wave amplitude, a maximum/max slope during systole, a ratio of maximum amplitude to minimum amplitude, or a heart rate variability from the waveform of the pulse 110*i*6**.

In one embodiment, a pulse wave of the subject may not have a dicrotic wave; therefore, the feature extraction unit 1122 may not extract feature(s) of a dicrotic wave from the waveform of the pulse **110*i*6. As an aortic valve is suddenly closed in the early ventricular diastole, blood may flow reversely, hit the aorta, and then rebound, which cause the aortic pressure to rise again. As a result, a dicrotic wave is formed. A dicrotic wave may serve as an alternative (measurement) to pulse transit time (PTT), but the diastolic time Dt1** may be used as an alternative (measurement) to pulse transit time as well.

The calculation unit 1124 may calculate a physiological index according to feature(s) extracted by the feature extraction unit 1122. The calculation unit 1124 may use (or base on) the feature(s) to build a model and find the physiological index using (or based on) the model.

In one embodiment, the calculation unit 1124 may estimate blood pressure by means of linear regression. Linear regression is a kind of regression model that uses known blood pressure and corresponding feature(s) to train/find an equation having minimal error (e.g., to calculate/find the slope and intercept). The equation having minimal error (whose unknown coefficients are estimated from data (points)) is able to approximate/fit to (the trend/distribution of) the data (points) so as to predict/infer blood pressure. In one embodiment, blood pressure(s) measured by a cuff-style blood pressure monitor, which serves/serve as known blood pressure(s), and feature(s) extracted from waveform(s) measured by Photoplethysmography may be used together to train the regression model. In one embodiment, the equation may be $Y=\alpha_0+\alpha_1 x_1+\alpha_2 x_2+ \ldots +\alpha_n x_n$, where Y denotes blood pressure (e.g., a known/unknown blood pressure), $x_1$-$x_n$ denote feature(s) input to the calculation unit 1124, $\alpha_1$-$\alpha_n$ denote equation coefficients obtained in the case of least square error. In other words, with proper equation coefficients $\alpha_1$-$\alpha_n$, and the equation may have the minimum sum of the squares of the residuals (or deviations/errors), which are the differences between the data (points) and corresponding fitted values given in the equation, from the given data (points).

In one embodiment, the calculation unit 1124 may select certain feature(s) through trial and error to make linear regression less error-prone. In one embodiment, the features selected by the calculation unit 1124 may be pulse transit time and heart rate. The relationship between blood pressure, pulse transit time and heart rate may satisfy BP=aPTT+bHR+c, where BP denotes blood pressure, PTT denotes pulse transit time, and HR denotes heart rate. The pulse transit time may be obtained according to the time difference between a peak of an electrocardiogram (ECG) waveform and a peak of a Photoplethysmography waveform. Since a peak of an ECG waveform is related to the contraction of the ventricle and a peak of a Photoplethysmography waveform is related to the contraction of the blood vessel, the pulse transit time (which is the transmission time of blood transmitted from the heart to the blood vessel to be measured) is related to blood pressure. In one embodiment (for example, without ECG information), the diastolic time may replace the pulse transit time. In other words, the features selected by the calculation unit 1124 may be diastolic time and heart rate. The relationship between estimated blood pressure, diastolic time and heart rate may be $\tilde{Y} \approx aDt+bHR+c$, where $\tilde{Y}$~~ denotes estimated blood pressure, and Dt denotes diastolic time.

In one embodiment, the calculation unit 1124 may establish prediction model(s) for diastolic blood pressure and systolic blood pressure, respectively. In one embodiment, the calculation unit 1124 may find/get a linear equation with a set of coefficients a, b, c for diastolic blood pressure and find/get another linear equation with another set of coefficients a, b, c for systolic blood pressure. The estimated diastolic blood pressure or systolic blood pressure may be obtained or solved by substituting/plugging-in the feature(s) into the corresponding linear equation.

In one embodiment, the calculation unit 1124 may find potential correlations between feature(s) and blood pressure(s) by means of machine learning. For example, (known) first data (e.g., feature(s) corresponding to a (known) blood pressure, which is/are extracted by the feature extraction unit 1122) may be put through an (untrained) model by the calculation unit 1124 in the training (stage) of machine learning. The calculation unit 1124 may compare the output of the model with the (known) blood pressure of the (known) first data. As a result, parameter(s) of the model may be re-evaluated/update and optimized to train the model and to minimize (total) error(s). The calculation unit 1124 may apply/use knowledge from the (trained) model to infer a result in the inference or prediction (stage) of machine learning. Accordingly, when the (unknown) second data to be interpreted/recognized (e.g., feature(s) extracted by the feature extraction unit 1122 without corresponding to a (known) blood pressure) is input through the (trained) model, the (trained) model may perform inference on the second data according to the (optimized) parameter(s) to generate its output prediction(s).

The output module 114 may output physiological index (e.g., systolic blood pressure or diastolic blood pressure) such as via image(s) popping up on a screen, via blinking light(s), or via sound produced from a speaker.

In one embodiment, if the length of a measurement time of the signal feature extraction device 10 for a subject exceeds a predetermined time length (for example, more than 20 seconds, but not limited to) but the template pulse 108*v* cannot be built (for example, the number of reference pulses in the reference waveform sequence cannot reach a preset pulse number within the predetermined time length), or if the number of pulses matching the template pulse 108*v* is less than a number threshold (for example, less than 4, but not limited to), the output module 114 may output a re-measurement message to remind/inform the subject to re-measure blood pressure and/or advise the subject to relax, rest, or adjust the wearing position to re-measure. Accordingly, the signal feature extraction device 10 may re-receive a signal from the ear-clip physiological measurement device.

In one embodiment, the input module 100, the preprocessing module 102, the local extreme value detection module 104, the waveform segmentation module 106, the template initialization module 108, the template matching module 110, the calculation module 112, the feature extraction unit 1122, the calculation unit 1124, or the output module 114 may include/correspond to a circuit. In one embodiment, the connection, order, or numbers of the input module 100, the preprocessing module 102, the local extreme value detection module 104, the waveform segmentation module 106, the template initialization module 108, the template matching module 110, the calculation module 112, the feature extraction unit 1122, the calculation unit 1124, and the output module 114 may be adjusted adaptively.

In addition, calculation of the cross-correlation coefficient is detailed as follows. First, a cross-correlation coefficient $\rho_{XY}[n]$, which represents the cross-correlation coefficient between the previous pulse Y (e.g., the pulse 107S2) and the pulse under analysis X (e.g., the pulse 107S3), may satisfy $$\max(\rho_{XY}[n]) = \max\left(\sum_{m=0}^{2f_s}(X_{norm}[m])(Y_{NROM}[m+n])\right),$$

where $X_{NORM}$ denotes the pulse under analysis (e.g., the pulse 107S3) after normalization, and $Y_{NROM}$ denotes the previous pulse (e.g., the pulse 107S2) after normalization.

To calculate a ratio of correlation, it may require to compare (the cross-correlation coefficient $\rho_{XY}[n]$) with the maximum cross-correlation coefficient that can be measured (e.g., an autocorrelation coefficient $\max(\rho_{YY}[n])$ of the previous pulse. The autocorrelation coefficient $\max(\rho_{YY}[n])$ may satisfy $$\max(\rho_{YY}[n]/2) = \left(\sum_{m=0}^{2f_s}(Y_{NROM}[m])^2\right)/2).$$

A cross-correlation coefficient $SQI_{xcorr}$ may be defined as $$SQI_{XCORR} = \frac{2\max(\rho_{XY})}{\max(\rho_{YY})}.$$

The cross-correlation coefficient $SQI_{xcorr}$ may be associated with a ratio of a cross-correlation coefficient between the pulse under analysis X (e.g., the pulse 107S3) and the previous pulse Y (e.g., the pulse 107S2) to an autocorrelation coefficient of the previous pulse Y (e.g., the pulse 107S2). If the correlation coefficient $SQI_{xcorr}$ is closer to 1, the pulse under analysis X is more similar/correlated to the previous pulse Y. If the correlation coefficient $SQI_{xcorr}$ is less close to 1, the pulse under analysis X is less similar/correlated to (or uncorrelated) the previous pulse Y.

As set forth above, if the cross-correlation coefficient between the previous pulse and the pulse under analysis is greater than the similarity threshold, the occurrence/possibility of analyzing waveforms in poor shape may decrease. The present invention may thus avoid false determination and reduce misjudgment rate.

The signal feature extraction device 10 of the present invention is an exemplary embodiment of the present invention, and those skilled in the art may readily make different substitutions and modifications. For example, the aforementioned embodiments are mainly described with and focus on estimating blood pressure; however, in other embodiments, other physiological index such as blood oxygen concentration may be calculated. The aforementioned embodiments are mainly described with the signal 100S sensed by the Photoplethysmography; however, in other embodiments, the signal feature extraction device 10 may process signals measured by various contact sensors (e.g., ECG), signals measured by various non-contact sensors (such as radar sensors), or various other signals.

Figure 7:
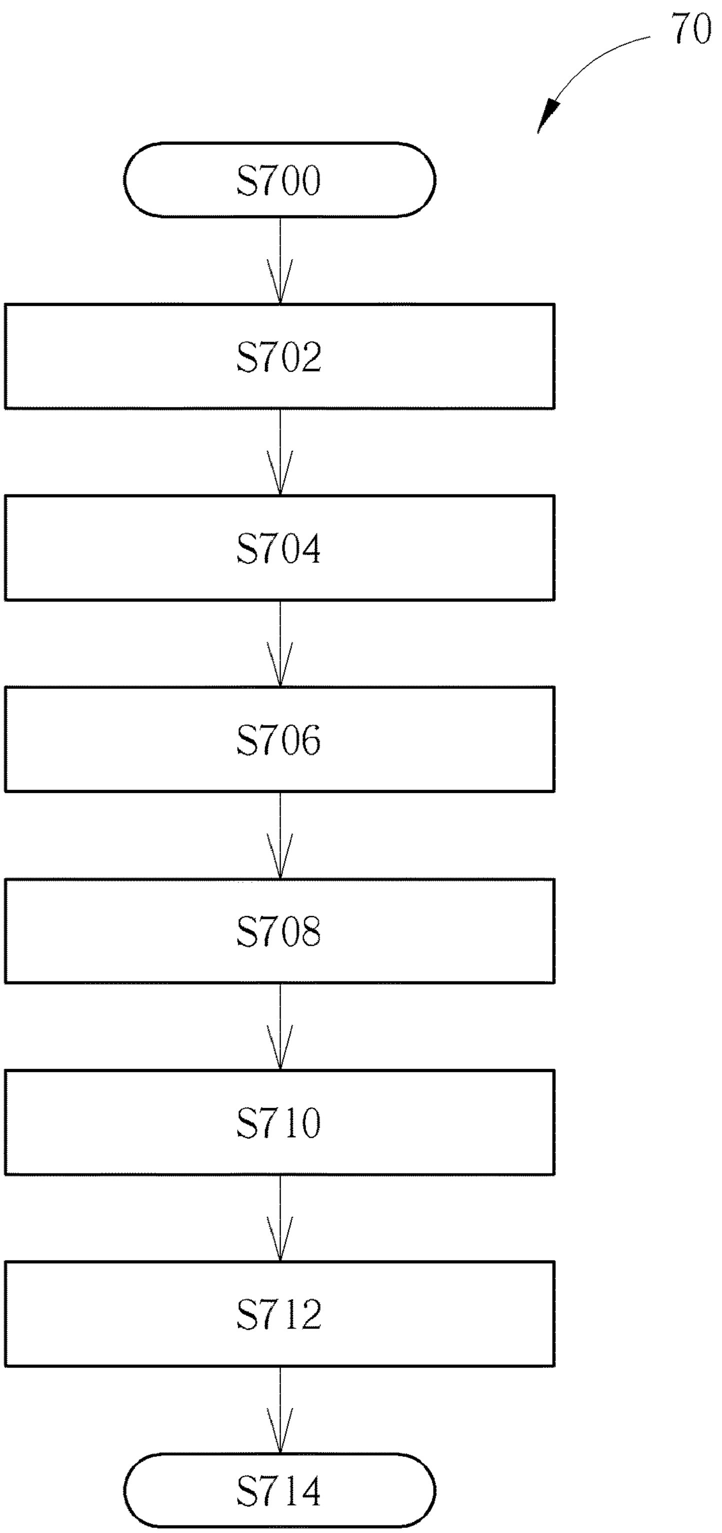
FIG. 7 to FIG. 8 are flowcharts of methods according to embodiments of the present invention.

FIG. 7 is a flowchart of a method 70 according to an embodiment of the present invention. The steps of the method 70 are as follows:

Step S700: Start.

Step S702: Receive a signal 100S, wherein the signal 100S includes a plurality of pulses.

Step S704: Determine in a situation that a second pulse in the plurality of pulses being correlated to a first pulse in the plurality of pulses.

Step S706: Select the second pulse as one of a plurality of reference pulses in a reference waveform sequence after the second pulse is determined as correlated to the first pulse.

Step S708: Average the plurality of reference pulses out to the template pulse 108*v*.

Step S710: Perform match comparison on the plurality of pulses by the template pulse respectively.

Step S712: Extract a plurality of features from each of the plurality of pulses, which matches the template pulse 108*v*.

Step S714: End.

The method 70 includes determining whether the second pulse in the plurality of pulses is similar/correlated to the first pulse in the plurality of pulses in Step S704, selecting the second pulse to be one of a plurality of reference pulses in a reference waveform sequence after the second pulse is deemed similar/correlated to the first pulse in Step S706, or determining whether any of the plurality of pulses matches the template 108*v* in Step S710.

In one embodiment, the second pulse follows/comes after the first pulse. (A start point or) an end point of the first pulse may or may not coincide with (an end point or) a start point of the second pulse. In one embodiment, the end point of the first pulse may coincide with a start point of a pulse train/series; an end point of the pulse train/series may coincide with the start point of the second pulse. The pulse train/series may include a plurality of pulses, which are successive and coming one after another without others coming in between.

In one embodiment, after determining whether the second pulse is similar/correlated to the first pulse, whether a third pulse in the plurality of pulses is similar/correlated to the second pulse may be determined. In response to a third pulse in the plurality of pulses is determined as correlated to the second pulse after the second pulse is determined as correlated to the first pulse. In one embodiment, whether any of the plurality of pulses is similar/correlated to another of the plurality of pulses may be determined one by one (namely, any two of the plurality of pulses are compared in succession) until the number of the plurality of reference pulses in the reference waveform sequence reaches a preset pulse number. Any of the plurality of pulses is determined as correlated to another of the plurality of pulses until the number of the plurality of reference pulses in the reference waveform sequence reaches the preset pulse number.

In one embodiment, one of the plurality of features may be a first time length between a first trough and a peak of one of the plurality of pulses, a second time length between the peak and a second trough of the pulse, the reciprocal of a third time length between the first trough and the second trough, the amplitude of the peak of the pulse, or a maximum/max slope between the first trough and the peak, but is not limited to this.

Figure 8:
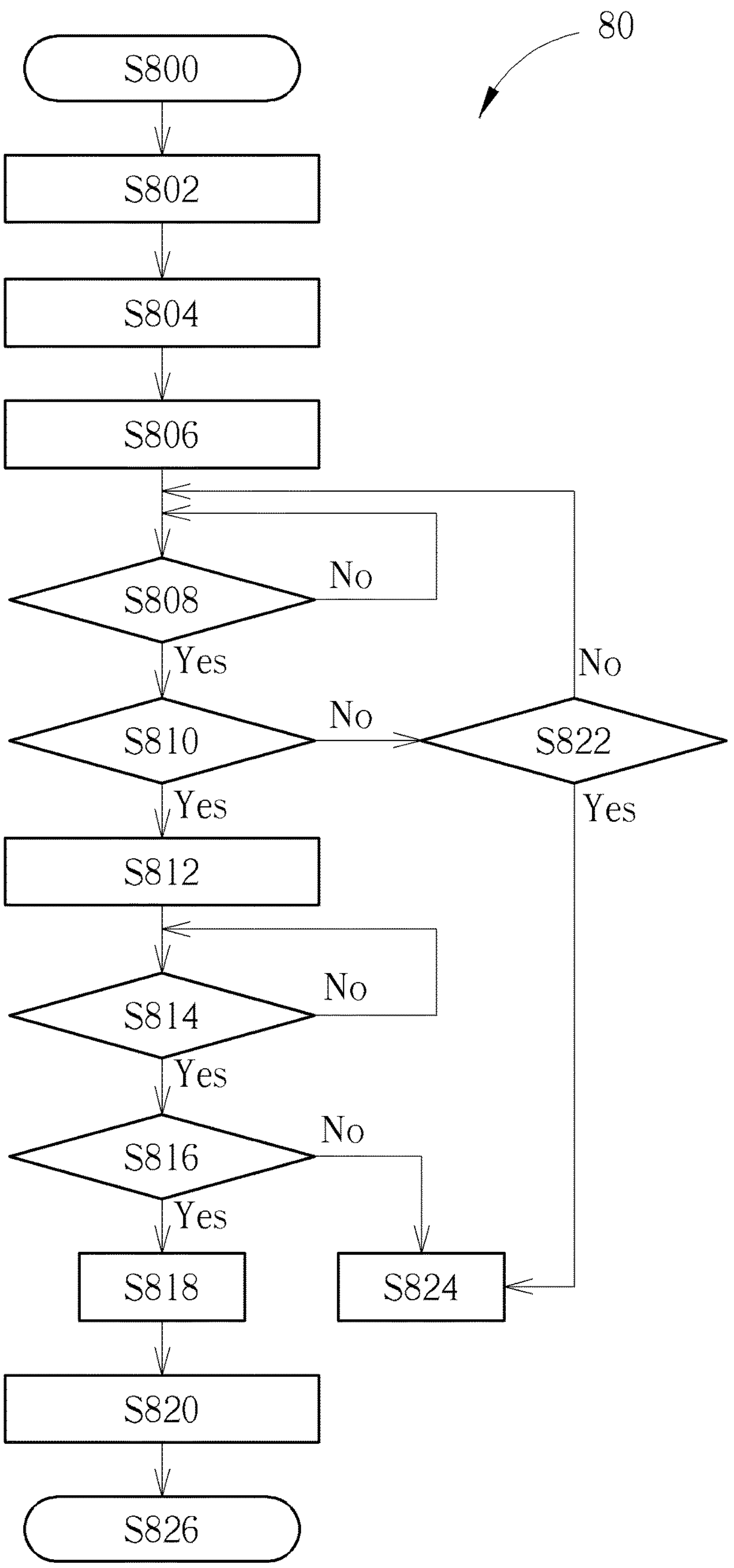

FIG. 8 is a flowchart of a method 80 according to an embodiment of the present invention. The steps of the method 80 are as follows:

Step S800: Start.

Step S802: Pre-process the signal 100S.

Step S804: Search for at least one local extreme value of the preprocessed signal 102S after pre-processing.

Step S806: Divide the waveform of the preprocessed signal 102S according to the at least one local extreme value to extract a plurality of pulses.

Step S808: Determine whether a previous pulse is similar/correlated to a pulse under analysis. If yes, go to Step S810; otherwise, replace the pulse under analysis with another and execute Step S808 again.

Step S810: Add the pulse under analysis to the reference waveform sequence, and determine whether the number of reference pulse(s) in the reference waveform sequence is equal to a preset pulse number. If yes, go to Step S812; otherwise, go to Step S822.

Step S812: Average the reference pulse(s) out to the template pulse 108*v*.

Step S814: Determine whether a pulse measured in a measurement time matches the template pulse 108*v*. If yes, go to Step S816; otherwise, replace the pulse under analysis with another and execute Step S814 again.

Step S816: Determine whether the number of pulse(s), which match/matches the template pulse 108*v*, is greater than a number threshold value. If yes, go to step S818; otherwise, go to Step S824.

Step S818: Extract feature(s) from the pulse(s), which match/matches the template pulse 108*v*.

Step S820: Calculate physiological index/indexes using the feature(s) having been extracted.

Step S822: Determine whether the number of reference pulse(s) in the reference waveform sequence is still less than a preset pulse number after a predetermined time length. If yes, go to Step S824; otherwise, go to Step S808.

Step S824: Suggest the subject performing measurement (with a measurement device) again.

Step S826: End.

The method 70 or 80 may be applied in the signal feature extraction device 10 of FIG. 1. The method 70 or 80 may be compiled into a program code executed by a processing circuit and stored in a storage circuit. One or more of Steps S702 to S712 in the method 70 or Steps S802 to S824 in the method 80 may be optional or omitted. The order of one or more of Steps S702-S712 in the method 70 or Steps S802-S824 in the method 80 may be reversed or swapped. The quality of the preprocessed signal 102S may be checked before Step S804.

To sum up, the signal feature extraction device of the present invention may perform signal processing (e.g., screening waveform(s) measured by a Photoplethysmography module) before feature extraction. The present invention may create a waveform template (e.g., the template pulse 108*v*) according to the similarity/correlation of continuous periodic pulse waves, and screen the waveform of signal(s) with the waveform template to make sure the selected pulse(s) in the present invention is good enough for blood pressure estimation (namely, ensure that waveform feature(s) for estimating blood pressure are correct/proper), thereby improving the accuracy of blood pressure measurement of Photoplethysmography. The present invention may use a Photoplethysmography module and a signal feature extraction device to monitor whether blood pressure rises or falls.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A physiological signal feature extraction method, comprising:

receiving, from a physiological measurement device, a physiological signal, wherein the physiological signal comprises a plurality of pulses;

calculating a normalized pulse duration according to a plurality of pulse time lengths of the plurality of pulses, wherein the normalized pulse duration is a median or a mode of the plurality of pulse time lengths;

adjusting each of the plurality of pulse time lengths of the plurality of pulses to the normalized pulse duration using down-sampling or up-sampling;

determining in a situation that a second pulse in the plurality of pulses is correlated to a first pulse in the plurality of pulses;

selecting the second pulse as one of a plurality of reference pulses in a reference waveform sequence after the second pulse is determined as correlated to the first pulse;

averaging the plurality of reference pulses out at a template pulse;

performing match comparison on the plurality of pulses by the template pulse respectively; and extracting a plurality of features from each of the plurality of pulses matching the template pulse.

2. The physiological signal feature extraction method of claim 1, wherein the step of determining in a situation that the second pulse being correlated to the first pulse comprises:

calculating a first cross-correlation coefficient between the second pulse and the first pulse;

determining the first pulse is correlated to the second pulse according to the first cross-correlation coefficient being greater than or equal to a similarity threshold; and determining the first pulse is uncorrelated to the second pulse according to the first cross-correlation coefficient being less than the similarity threshold.

3. The physiological signal feature extraction method of claim 1, wherein the second pulse follows the first pulse, and an end point of the first pulse coincides with a start point of the second pulse.

4. The physiological signal feature extraction method of claim 1, wherein a third pulse in the plurality of pulses is determined as correlated to the second pulse after the second pulse is determined as correlated to the first pulse.

5. The physiological signal feature extraction method of claim 1, wherein any of the plurality of pulses is determined as correlated to another of the plurality of pulses until a number of the plurality of reference pulses in the reference waveform sequence reaches a preset pulse number.

6. The physiological signal feature extraction method of claim 1, wherein the step of determining in a situation that the plurality of pulses match the template pulse respectively comprises:

calculating a second cross-correlation coefficient between one of the plurality of pulses and the template pulse;

determining the pulse matches the template pulse according to the second cross-correlation coefficient being greater than or equal to a match threshold; and determining the pulse mismatches the template pulse according to the second cross-correlation coefficient being less than the match threshold.

7. The physiological signal feature extraction method of claim 1, wherein one of the plurality of features is a first time length between a first trough and a peak of one of the plurality of pulses, a second time length between the peak and a second trough of the pulse, a reciprocal of a third time length between the first trough and the second trough, an amplitude of the peak of the pulse, or a max slope between the first trough and the peak.

8. The physiological signal feature extraction method of claim 1, further comprising:

building a model based on the plurality of features; and calculating a physiological index based on the model, wherein the model is trained according to machine learning to optimize a parameter of the model.

9. The physiological signal feature extraction method of claim 1, wherein another physiological signal is required to be retransmitted after a number of one or more of the plurality of pulses matching the template pulse is determined as less than a number threshold or after a number of the plurality of reference pulses fails to reach a preset pulse number within a predetermined time length.

10. A physiological signal feature extraction device, comprising:

a processing circuit, for executing a program code; and a storage circuit, coupled to the processing circuit and for storing the program code, wherein the program code comprises:

receiving, from a physiological measurement device, a physiological signal, wherein the physiological signal comprises a plurality of pulses;

calculating a normalized pulse duration according to a plurality of pulse time lengths of the plurality of pulses, wherein the normalized pulse duration is a median or a mode of the plurality of pulse time lengths;

adjusting each of the plurality of pulse time lengths of the plurality of pulses to the normalized pulse duration using down-sampling or up-sampling;

determining in a situation that a second pulse in the plurality of pulses is correlated to a first pulse in the plurality of pulses;

selecting the second pulse as one of a plurality of reference pulses in a reference waveform sequence after the second pulse is determined as correlated to the first pulse;

averaging the plurality of reference pulses out at a template pulse;

performing match comparison on the plurality of pulses by the template pulse respectively; and extracting a plurality of features from each of the plurality of pulses matching the template pulse.

11. The physiological signal feature extraction device of claim 10, wherein the step of determining in a situation that the second pulse being correlated to the first pulse comprises:

calculating a first cross-correlation coefficient between the second pulse and the first pulse;

determining the first pulse is correlated to the second pulse according to the first cross-correlation coefficient being greater than or equal to a similarity threshold; and determining the first pulse is uncorrelated to the second pulse according to the first cross-correlation coefficient being less than the similarity threshold.

12. The physiological signal feature extraction device of claim 10, wherein the second pulse follows the first pulse, and an end point of the first pulse coincides with a start point of the second pulse.

13. The physiological signal feature extraction device of claim 10, wherein a third pulse in the plurality of pulses is determined as correlated to the second pulse after the second pulse is determined as correlated to the first pulse.

14. The physiological signal feature extraction device of claim 10, wherein any of the plurality of pulses is determined as correlated to another of the plurality of pulses until a number of the plurality of reference pulses in the reference waveform sequence reaches a preset pulse number.

15. The physiological signal feature extraction device of claim 10, wherein the step of determining in a situation that the plurality of pulses match the template pulse respectively comprises:

calculating a second cross-correlation coefficient between one of the plurality of pulses and the template pulse;

determining the pulse matches the template pulse according to the second cross-correlation coefficient being greater than or equal to a match threshold; and determining the pulse mismatches the template pulse according to the second cross-correlation coefficient being less than the match threshold.

16. The physiological signal feature extraction device of claim 10, wherein one of the plurality of features is a first time length between a first trough and a peak of one of the plurality of pulses, a second time length between the peak and a second trough of the pulse, a reciprocal of a third time length between the first trough and the second trough, an amplitude of the peak of the pulse, or a max slope between the first trough and the peak.

17. The physiological signal feature extraction device of claim 10, wherein the program code further comprises:

building a model based on the plurality of features; and calculating a physiological index based on the model, wherein the model is trained according to machine learning to optimize a parameter of the model.

18. The physiological signal feature extraction device of claim 10, wherein another physiological signal is required to be retransmitted after a number of one or more of the plurality of pulses matching the template pulse is determined as less than a number threshold or after a number of the plurality of reference pulses fails to reach a preset pulse number within a predetermined time length.

* * * * *